(12) United States Patent
Lafitte et al.

(10) Patent No.: US 9,377,434 B2
(45) Date of Patent: Jun. 28, 2016

(54) ELECTRO-CHEMICAL SENSOR

(75) Inventors: Valerie Lafitte, Stafford, TX (US);
Nathan S. Lawrence, Wyton (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 100 days.

(21) Appl. No.: 13/502,718

(22) PCT Filed: Oct. 14, 2010

(86) PCT No.: PCT/IB2010/002641
§ 371 (c)(1),
(2), (4) Date: Jul. 9, 2012

(87) PCT Pub. No.: WO2011/070408
PCT Pub. Date: Jun. 16, 2011

(65) Prior Publication Data
US 2012/0268134 A1    Oct. 25, 2012

(30) Foreign Application Priority Data

Dec. 9, 2009 (GB) .................................. 0921511.2

(51) Int. Cl.
*G01N 27/403* (2006.01)
*G01N 27/416* (2006.01)
(Continued)

(52) U.S. Cl.
CPC ............. *G01N 27/3335* (2013.01); *G01N 33/18* (2013.01)

(58) Field of Classification Search
CPC ............. G01N 27/3335; G01N 27/126; G01N 27/308; G01N 27/302; G01N 33/18; G01N 33/84; G01N 33/5438; E21B 47/01; E21B 47/10; E21B 49/08; E21B 49/10; C12Q 1/001

USPC .......... 324/324, 325, 353; 204/400, 407, 418, 204/431, 433, 435; 205/789, 788, 792
See application file for complete search history.

(56) References Cited

U.S. PATENT DOCUMENTS 4,986,354 A   1/1991  Cantu et al.
5,223,117 A   6/1993  Wrighton et al.
(Continued)

FOREIGN PATENT DOCUMENTS

GB   2337332 A   11/1999
GB   2430749 A    4/2007
(Continued)

OTHER PUBLICATIONS

Combined Search and Examination Report of British Application Serial No. GB 0921511.2 dated Feb. 9, 2010.
(Continued)

*Primary Examiner* — Tung X Nguyen
*Assistant Examiner* — David Frederiksen

(57) ABSTRACT

An electrochemical sensor for the presence or concentration of an analyte has at least one electrode and at least one electrochemically active species able to undergo electrochemical reaction in response to electrical potential applied to the electrode, where the said reaction is modified by the presence of the analyte. This sensor has the novel characteristic that at least one said electrochemically active species is encapsulated within polymer particles. These particles are preferably formed from an amorphous polymer with a glass transition temperature above the temperature of the fluid to which the sensor is exposed. The encapsulating polymer protects the analyte species from degradation, but a small analyte such as a hydrogen or bisulfide ion can pass through the polymer and undergo reaction at the active species.

18 Claims, 5 Drawing Sheets

(51) Int. Cl.
*G01V 3/18* (2006.01)
*G01N 27/333* (2006.01)
*G01N 33/18* (2006.01)

(56) References Cited

U.S. PATENT DOCUMENTS

| | | | |
|---|---|---|---|
| 6,484,046 B1* | 11/2002 | Say | A61B 5/14532 600/309 |
| 6,730,212 B1 | 5/2004 | Yamagishi et al. | |
| 6,770,190 B1* | 8/2004 | Milanovski | G01N 33/5438 205/777.5 |
| 7,611,621 B2 | 11/2009 | Cai et al. | |
| 8,177,958 B2* | 5/2012 | Lawrence et al. | 205/787.5 |
| 2003/0130167 A1* | 7/2003 | Pitner et al. | 514/2 |
| 2004/0149577 A1 | 8/2004 | Kumar et al. | |
| 2004/0155211 A1 | 8/2004 | Takeda et al. | |
| 2004/0176732 A1* | 9/2004 | Frazier et al. | 604/345 |
| 2004/0182719 A1* | 9/2004 | Purvis et al. | 205/414 |
| 2005/0211572 A1* | 9/2005 | Buck et al. | 205/778 |
| 2005/0241382 A1* | 11/2005 | Coenen | 73/152.19 |
| 2007/0000338 A1* | 1/2007 | Brumboiu et al. | 73/866.5 |
| 2007/0146715 A1* | 6/2007 | Potyrailo et al. | 356/432 |
| 2007/0251829 A1* | 11/2007 | Marsh | 205/343 |
| 2008/0029391 A1 | 2/2008 | Mao et al. | |
| 2008/0255309 A1* | 10/2008 | Weinberg et al. | 525/148 |
| 2008/0293997 A1* | 11/2008 | Buhlmann et al. | 600/17 |
| 2009/0014325 A1* | 1/2009 | Jones et al. | 204/400 |
| 2009/0178921 A1 | 7/2009 | Lawrence et al. | |
| 2009/0242399 A1* | 10/2009 | Kamath | A61B 5/14532 204/403.1 |

FOREIGN PATENT DOCUMENTS

| | | | |
|---|---|---|---|
| WO | 9322537 | A1 | 11/1993 |
| WO | 03106809 | A1 | 12/2003 |
| WO | 2005066618 | A1 | 7/2005 |
| WO | 2005081653 | A2 | 9/2005 |
| WO | 2007034131 | A1 | 3/2007 |

OTHER PUBLICATIONS

International Search Report of PCT Application No. PCT/IB2010/002641 dated Aug. 1, 2011.
Wildgoose et al., "Abrasively Immmobilised Multiwalled Carbon Nanotube Agglomerates: A Novel Electrode Material Approach for the Analytical Sensing of pH," ChemPhysChem, 2004, vol. 5: pp. 669-677.
Giovanelli et al., "Amperometric determination of sulfide at a pre-oxidised nickel electrode in acidic media," Analyst, 2003, vol. 128: pp. 173-177.
Wildgoose et al., "Anthraquinone-derivatised carbon powder: reagentless voltammetric pH electrodes," Talanta, 2003, vol. 60: pp. 887-893.
Palleschi et al., "Bioelectrochemical Determination of Lactic and Malic Acids in Wine," Talanta, 1994, vol. 41(6): pp. 917-923.
Jasat et al., "Carceplexes and Hemicarceplexes," Chemical Reviews, Apr. 1999, vol. 99(4): pp. 931-967.
Dandliker et al., "Dendritic Porphyrins: Modulating Redox Potentials of Electroactive Chromophores with Pendant Multifunctionality," Angew. Chem. Int. Ed. Engl., 1994, vol. 33 (17): pp. 1739-1742.
Leventis et al., "Derivatised carbon powder electrodes: reagentless pH sensors," Talanta, 2004, vol. 63: pp. 1039-1051.
Bard et al., Electrochemical Methods: Fundamentals and Applications, New York: John Wiley & Sons, Inc., Second Edition, 2001: pp. 226-252, 275, 293-301 and 640-644.
Cardona et al., "Electrochemistry of encapsulated redox centers," Chem. Soc. Rev., 2000, vol. 29: pp. 37-42.
Aquino et al., "Fabrication and Characterization of a Hydroquinone-Functionalized Polypyrrole Thin-Film pH Sensor," Chem. Mater., 1996, vol. 8: pp. 2579-2585.
Podkoscielny et al., "Ferrocene Derivatives Included in a Water-Soluble Cavitand: Are They Electroinactive?" Organic Letters, 2008, vol. 10(13): pp. 2865-2868.
Baucke, "The Glass Electrode—Applied Electrochemistry of Glass Surfaces," Journal of Non-Crystalline Solids, 1985, vol. 73: pp. 215-231.
Pandurangappa et al., "Homogeneous chemical derivatisation of carbon particles: a novel method for funtionalising carbon surfaces," Analyst, 2002, vol. 127: pp. 1568-1571.
Hickman et al., "Molecular Self-Assembly of Two-Terminal, Voltammetric Microsensors with Internal References," Science, Reports, May 1991, vol. 252: pp. 688-691.
Komaba et al., "Potentiometric biosensor for urea based on electropolymerized electoinactive polypyrrole," Electrochimica Acta, 1997, vol. 42(3): pp. 383-388.
Janata, "Potentiometric Microsensors," Chem. Rev., 1990, vol. 90: pp. 691-703.
Conn et al., "Self-Assembling Capsules," Chem. Rev., 1997, vol. 97: pp. 1647-1668.
Streeter et al., "A sensitive reagentless pH prove with a ca. 120 mV/pH unit response," J Solid State Electrochem, 2004, vol. 8: pp. 718-721.
Ben-David et al., "Simple Absorption Optical Fiber pH Sensor Based on Doped Sol-Gel Cladding Material," Chem. Mater., 1997, vol. 9: pp. 2255-2257.
Robinson et al., "Sulfide sensing via differential counter ion diffusion rates through redox-modulated poly (vinylferrocene) microparticles," Electrochemistry Communications, 2006, vol. 8: pp. 1055-1061.
Balzani et al., "Switching of Pseudorotaxanes and Catenanes Incorporating a Tetrathiafulvalene Unit by Redox and Chemical Inputs," J. Org. Chem., 2000, vol. 65: pp. 1924-1936.
Tustin et al., "Synthesis and characterisation of water soluble ferrocenes: Molecular tuning of redox potentials," Journal of Organometallic Chemistry, 2007, vol. 692: pp. 5173-5182.
Lawrence et al., "Triple Component Carbon Epoxy pH Probe," Electroanalysis, 2007, vol. 19(4): pp. 424-428.
Lawrence et al., "Voltammetric Characterization of a N,N'-Diphenyl-p-phenylenediamine-Loaded Screen-Printed Electrode: A Disposable Sensor for Hydrogen Sulfide," Anal. Chem., May 2003, vol. 75(9): pp. 2054-2059.

\* cited by examiner

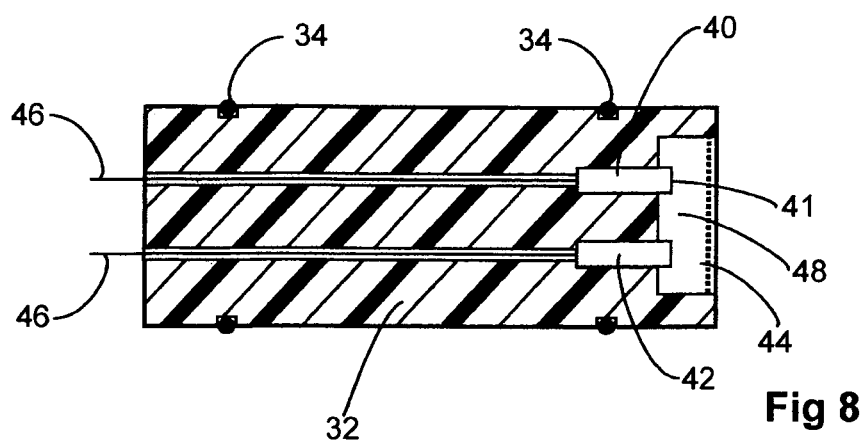
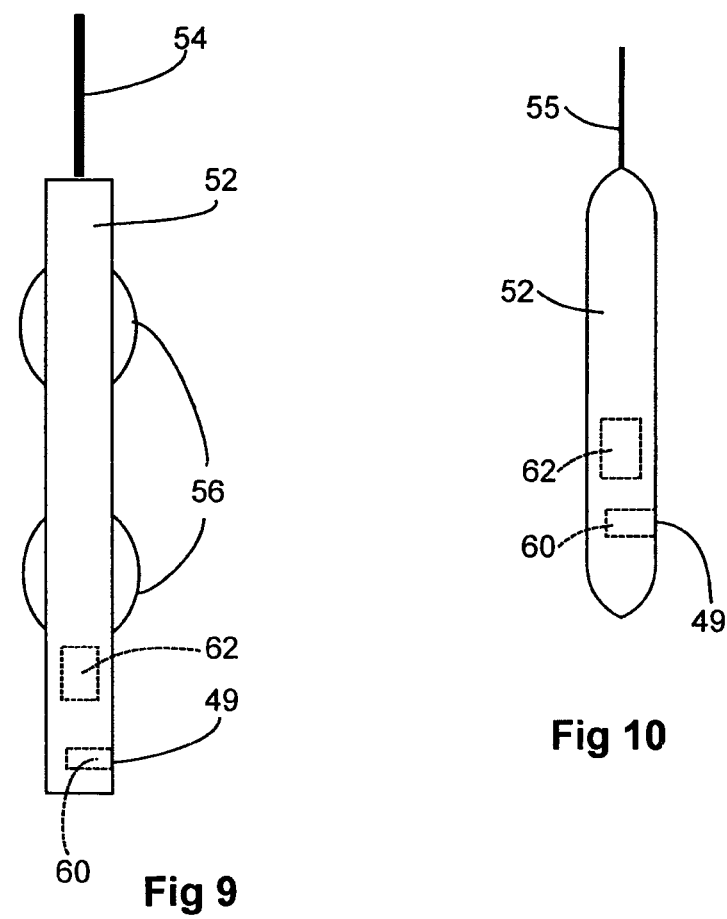

ELECTRO-CHEMICAL SENSOR

FIELD OF THE INVENTION

This invention relates to electrochemical sensors for determining constituents of fluids. Fields in which the invention may be utilised include, although are not restricted to, the analysis of aqueous fluid at the Earth's surface, including aqueous fluid which is about to be pumped to a subterranean location and also the analysis of subterranean fluids which may be in an aquifer, in a hydrocarbon reservoir or in a carbon dioxide sequestration facility.

BACKGROUND OF THE INVENTION

There are numerous circumstances in which it is desirable to detect, measure or monitor a constituent of a fluid. One of the commonest requirements is to determine hydrogen ion concentration (generally expressed on the logarithmic pH scale) of aqueous fluids which may for example be a water supply or an effluent. The determination of the pH of a solution is one of the most common analytical measurements and can be regarded as the most critical parameter in water chemistry. Nearly all water samples will have their pH tested at some point in their life cycle as many chemical processes are dependent on pH. Another common requirement is to determine oxygen content in water.

A particularly challenging context is the analysis of downhole fluids, that is to say fluids encountered at underground locations accessed by a wellbore. In the context of hydrocarbon production, analysis of downhole fluids can be an important aspect of determining the quality and economic value of a hydrocarbon formation. Knowledge of downhole formation (produced) water chemistry can be applied to save costs and increase production at all stages of oil and gas exploration and production. Measurements obtained downhole can be important for a number of key processes of hydrocarbon production, including:

Prediction and assessment of mineral scale and corrosion;
Strategy for oil/water separation and water re-injection;
Understanding of reservoir compartmentalization/flow units;
Characterization of water break-through;
Derivation of the water cut $R_w$; and
Evaluation of downhole $H_2S$ partition in the oil and or water (if used for $H_2S$ measurements).

Some chemical species dissolved in water (for example, $Cl^-$ and $Na^+$) do not change their concentration when moved to the surface either as a part of a flow through a well, or as a sample taken downhole. Consequently information about their quantities may be obtained from downhole samples and in some cases surface samples of a flow. However, the state of chemical species, such as $H^+$ (noting that pH=−log [concentration of $H^+$]), $CO_2$, or $H_2S$ may change significantly while tripping to the surface. The change occurs mainly due to a difference in temperature and pressure between downhole and surface environment. In case of samples taken downhole, this change may also happen due to degassing of a sample (seal failure), mineral precipitation in a sampling bottle, and (especially in case of $H_2S$)—a chemical reaction with the sampling chamber. It should be stressed that, in the field of hydrocarbon production, pH, $H_2S$, and $CO_2$ are among the most critical parameters for corrosion and scale assessment. Consequently it is of considerable importance to determine their downhole values and there have been a number of proposals for analytical sensors to be used downhole. However, the downhole environment is apt to be chemically aggressive and the lifetime and stability of sensors is an issue. Whilst hydrocarbon production is an area of application of considerable significance, parallel issues arise when investigating downhole fluids in other circumstances.

One approach to the construction of sensors to be used below the Earth's surface makes use of an electrochemical reaction brought about by the application of potential to electrodes, where the electrochemical response is altered by the presence of an analyte species and in consequence the alteration in the electrochemical response serves as a measure of the concentration of the analyte species.

An electrochemical sensor may then comprise electrodes and one or more electrochemically active species able to undergo electrochemical reaction in response to electrical potential applied to the electrodes, where that electrochemical reaction is modified by the presence of an analyte species.

One example of an electrochemical pH sensor is disclosed in U.S. Pat. No. 5,223,117, where the sensor was intended for use in a number of applications including biomedical sensing. Two electrochemically active species were attached to a gold substrate which provided an electrode. Both of these attached species were redox systems. One of the attached species was hydroquinone whose redox potential is sensitive to the concentration of hydrogen ions while the other attached species was ferrocene which serves as a reference because its redox potential is insensitive to hydrogen ion concentration. This sensor was used in voltammetry in which the gold substrate with the attached redox systems and the counter electrode are placed in contact with a solution to be tested. The potential applied to the gold substrate was systematically varied and current flow was monitored. With such a system, a plot of current against applied voltage, a so-called voltammogram, shows current peaks when the applied voltage is such that the redox reactions take place. The voltage difference between the voltage giving peak current for the ferrocene reference and the voltage giving peak current for hydroquinone provides a measure of the pH of the solution under test.

Examples of sensors intended to be suitable for use downhole, incorporating electrodes and electrochemically active species, are described in WO 2005/066618 and WO 2007/034131. These documents envisage immobilizing redox systems on a conductive carbon substrate. In the latter document, two redox systems were incorporated chemically into a copolymer made from vinyl ferrocene and vinyl anthracene so that the two redox systems were present as side chains from the hydrocarbon backbone of the polymer. This fixed their proportions relative to each other. However, problems have been found to arise when redox systems are attached to macromolecules. The vast majority of polymers have transition temperatures above which the physical properties of the polymer alter. There is a loss of physical stability, which can be profoundly detrimental to the ability of a polymer to act as a sensor. Secondly, when redox systems are distributed along a polymer chain, it is possible for an electron to hop from one redox centre to the next along the chain, interfering with reversibility of the redox reaction. This phenomenon has been demonstrated in particular for polyvinyl ferrocene and its derivatives, where it was found that the cyclic voltammetric response can be sensitive not only to the analyte of interest but also to the concentration of other anions in solution, with decays in signal observed in the presence of certain anions (see K. L. Robinson and N. S. Lawrence, Electrochem. Commun., vol 8 page 1005 (2006).

SUMMARY OF THE INVENTION

Broadly, the present invention is concerned with an electrochemical analytical procedure involving a chemical which participates in electrochemical reaction, characterized in that the chemical is encapsulated with polymer particles.

In one aspect the present invention provides an electrochemical sensor comprising at least one electrode and one or more electrochemically active species able to undergo electrochemical reaction in response to electrical potential applied to the electrode(s), said reaction being modified by the presence of an analyte species, characterised in that at least one said electrochemically active species is encapsulated within polymer particles. The invention also includes equipment such as a wireline tool, incorporating such a sensor. This equipment may be configured and intended for use downhole.

Other electrodes which are required when carrying out the electrochemical reaction may be provided separately, or may be incorporated into the sensor.

The polymer particles in which the encapsulated electrochemically active species is immobilized could be free to move about within a quantity of electrolyte in contact with the electrodes. However, it is preferred that they are immobilized relative to the sensor. So the sensor may comprise a solid substrate, which may be a body part of the sensor, to which the encapsulated electrochemically active species is immobilised. The sensor may provide an electrically insulating solid substrate to which the encapsulated species is immobilised, with the sensor having a conductive electrode in proximity to the encapsulated species. Or, the sensor may have an electrode which is formed by a conductive solid body on which at least one encapsulated electrochemically active species is immobilised.

An electrode may be provided by a solid, electrically conductive substrate on which at least one encapsulated electrochemically active species is immobilised.

This invention is not limited to a specific electrochemical reaction or category of reaction. However, the electrochemical change may be oxidation and/or reduction and such a redox reaction may be a change in oxidation state brought about by electron transfer. The one or more electrochemically active species may therefore be one or more redox systems, i.e. molecules capable of undergoing oxidation and reduction reactions, preferably reversible oxidation and reduction reactions, brought about through application of electrical potential.

We have observed that redox reactions can take place even when the species undergoing the reaction is enclosed within a polymeric matrix and thereby protected from its environment. Moreover, if the concentration of a small analyte molecule modifies the reaction, the effect of these analyte molecules can be observed even though the reacting species is enclosed within encapsulating polymer. Without being limited to theory, we attribute this to small ions being able to pass through encapsulating polymer while larger molecules are unable to do so.

The encapsulating polymer may be chosen such that it incorporates aromatic groups and/or heteroatoms which facilitate electron transfer to and from the encapsulated species.

It is desirable that the encapsulating polymer is at least partially amorphous and is below its glass transition temperature when it is at a location, notably at a subterranean location, where measurements are to be made. Accordingly, in a further aspect, this invention provides a method of measuring an analyte concentration in a fluid, which may be a wellbore fluid, comprising exposing a sensor embodying the invention to the fluid, where the encapsulating polymer in the sensor has a glass transition temperature above the temperature of the fluid. The method will then generally also include operating the sensor by applying electrical potential and observing current flow.

Glass transition temperature, denoted Tg, is a characteristic of amorphous materials. Many polymers have a solid appearance at ambient temperature, but are in fact wholly or partially in an amorphous glassy state. A glass is a liquid which is undercooled (sometimes termed supercooled) significantly below its true melting point and which has an extremely high viscosity. In a glass, most diffusive processes other than the movement of some very small molecules, take place at extremely low rates, such as microns per year.

When the temperature of a glass rises above its glass transition temperature Tg, the viscosity drops rapidly and the glass turns into a rubber, then as temperature increases further it turns into a deformable plastic which at even higher temperatures turns into a fluid. Tg is a parameter which is used in many areas of science and industry. Tg values can be determined using a differential scanning calorimeter and can be detected as a point at which a plot of heat input against temperature passes through an inflection point, thus giving a maximum of the first temperature derivative. When measuring Tg it is generally found desirable to operate the differential scanning calorimeter at a temperature ramp rate between 5 and 10° C. per minute.

We have found that an encapsulating polymer matrix becomes permeable when the particle is heated above Tg of the polymer and the enclosed material may then become more exposed to the fluid outside the polymer particles and/or the enclosed material may escape into the surrounding fluid and be lost.

Since subterranean temperatures are usually higher than those at the earth's surface, it may be desirable that Tg of the encapsulating polymer is well above ambient temperature at the surface. A Tg of at least 60° C. may be preferred, and possibly at least 80° C. or even at least 100° C. or 120° C.

A number of technologies are known for the encapsulation of one material within another material. Polymers have frequently been used as the encapsulating materials. Some examples of documents which describe encapsulation procedures are U.S. Pat. No. 4,986,354, WO 93/22537, and WO 03/106809.

Encapsulation of one material within another, in the present case encapsulation of an electrochemically active species within a polymer, can lead to particles in which the said species is distributed within a particle of the polymer, for instance as a plurality of small islands of the electrochemically active species surrounded by a continuous matrix of the polymer. Alternatively encapsulation can lead to core-shell type particles in which a core of the electrochemically active species is encapsulated within a shell of the polymer. Both core-shell and islands-in-matrix type particles may be used in this invention, although islands-in-matrix type particles may be preferred as giving a higher surface area of the encapsulated electrochemically active species.

We have found that electrochemically active species can be successfully encapsulated by processes which involve evaporation of solvent from an emulsified phase. Moreover, such processes are repeatable from batch to batch, allow the size of particles to be controlled and give an acceptably narrow distribution of particle size.

Hydrophobic electrochemically active species, soluble in organic solvent, can be encapsulated within a polymer using a technique comprising steps of (i) dissolving the electrochemically active species and encapsulating polymer in a water-immiscible organic solvent, (ii) dispersing the resulting solution in an aqueous phase to form an oil-in-water emulsion in which the disperse phase is the solution formed in step (i), (iii) stirring or otherwise agitating that emulsion while causing or allowing evaporation of the organic solvent, thereby forming particles in which the electrochemically active species is enclosed by the polymer.

Hydrophilic, water-soluble electrochemically active species can be encapsulated by a double emulsion technique. This comprises steps of (i) dissolving the electrochemically active species in water, (ii) dissolving the encapsulating polymer in a water-immiscible organic solvent, (iii) dispersing the aqueous solution of the electrochemically active species in the solvent solution of polymer to form a water-in-oil emulsion, (iv) dispersing this water-in-oil emulsion in water to form a water-in-oil-in-water double emulsion, and (iv) stirring or otherwise agitating that emulsion while causing or allowing evaporation of the organic solvent, thereby forming particles in which the electrochemically active species is enclosed by the polymer.

In the event that a required electrochemically active species is an insoluble solid in powder form, it can be encapsulated in an analogous way by (i) dissolving encapsulating polymer in organic solvent, (ii) suspending the substance to be encapsulated in the solvent solution of polymer in organic solvent, (iii) dispersing the resulting suspension in water, to form an emulsion in which the disperse phase is droplets of the organic solvent with the electrochemically active species to be encapsulated suspended within these droplets, and (iv) stirring or otherwise agitating that emulsion while causing or allowing evaporation of the organic solvent, thereby forming particles in which the electrochemically active species is enclosed by the polymer.

In each of these procedures the particle size is dependant on factors which include the choice of encapsulating polymer and the initial concentration of polymer in organic solvent, because these factors affect the viscosity of the disperse phase, from which organic solvent evaporates. A higher viscosity of this disperse phase leads to larger disperse droplets which in turn leads to larger particles. However, for any chosen composition, the droplet size of the disperse phase (and hence the particle size of the resulting polymer particles enclosing the electrochemically active species) can be controlled through the amount of shear applied to stir or agitate the emulsion while solvent evaporates. So, after choosing the encapsulating polymer and the other features of the composition, the significant parameters influencing particle size are the mixing condition and speed. We have found that it is possible to make particles with median particle sizes $d_{50}$ within a range from 50 to 250 micron. Particle size distribution may be such that $d_{10}$ is not less than 1 micron, and possibly not less than 20 micron while $d_{90}$ is not more than 500 micron, possibly not more than 300 micron.

All the above procedures lead to an aqueous suspension of particles comprising electrochemically active species encapsulated within polymer. The particles can be recovered by filtration, washed, dried and stored until required for use.

A number of materials have been proposed as redox systems for use in sensors. These include quinone, reversibly reducible to hydroquinone, and other aromatic diones such as anthraquinone which are similarly reversibly reducible to analogues of hydroquinone, N,N'-diphenyl-p-phenylenediamine and other substituted phenylene diamines, and ferrocene, various organo-substituted ferrocenes and other metallocenes.

A sensor embodying this invention may comprise two or more electrochemically active species with different sensitivities to analyte ions. There could example be one redox system which is sensitive to an analyte and a second redox system which is insensitive to that analyte and serves as an internal reference. One example of such a combination of two redox systems is anthraquinone as a pH sensitive redox system and ferrocene as a pH-independent reference. Another possibility is that there could be one species sensitive to one analyte and a second, different species sensitive to another analyte: for instance one species sensitive to hydrogen ion concentration, for measuring pH and a second species sensitive to the bisulfide ($HS^-$) ion, for measuring hydrogen sulfide concentration.

Where there is more than one electrochemically active species present, it is possible that they could be encapsulated within separate polymer particles, but it is also possible that the two species could be mixed together and then encapsulated. It is also within the scope of this invention that one electrochemically active species which is present is encapsulated while another is not.

In this invention the encapsulated electrochemically active species must of course be positioned where it (or they) can participate in electrochemical reaction. One possibility is that the particles of the encapsulated electrochemically active species may be immobilised on an electrically conductive solid body which is the working electrode, with that electrode and at least one other electrode immersed in a conductive solution, which could be an aqueous solution containing dissolved electrolyte.

This working electrode should not be chemically degraded by the fluid to which it is exposed. Noble metals have traditionally been used for electrodes, and may possibly be used in this invention, especially if the sensor is to be used to measure pH in a context where hydrogen sulfide is absent. However, in some embodiments of this invention the substrate is provided by elemental carbon, which is not susceptible to attack by sulfides or thiol groups.

The most common forms of conducting carbon used in electrode manufacture are glassy carbon, carbon fibres, carbon black, various forms of graphite, carbon paste, boron doped diamond and carbon epoxy. One further form of carbon, which has seen a large expansion in its use in the field of electrochemistry since its discovery in 1991 is the carbon nanotube (CNT). The structure of CNTs approximates to rolled-up sheets of graphite and can be formed as either single or multi-walled tubes. Single-walled carbon nanotubes (SWCNTs) constitute a single, hollow graphite tube. Multi-walled carbon nanotubes (MWCNTs) on the other hand consist of several concentric tubes fitted one inside the other.

Polymer particles may be immobilised on a hard surface by abrasion of the surface followed by rubbing the polymer particles onto the surface and into the surface abrasions.

It is also possible that polymer particles with reactive functional groups at a surface might be chemically immobilised onto an electrode.

Another possibility is that the polymer particles may be mixed with conductive carbon powder, mixed with a liquid to form a paste and the mixture packed into a holder which is part of the sensor and which exposes a surface at which there are both polymer particles and carbon particles. In this case the carbon particles provide the working electrode and there must be an electrical connection to them. An insulating body of the sensor may provide the holder and support an electrical connection to the paste packed into the holder.

The sensor might be constructed such that the electrochemical reaction can be followed by voltammetry. The sensor may then constitute at least part of a potentiometric cell with the electrodes and the encapsulated species in contact with the solution. In such a cell there will be a working electrode, also termed a measuring electrode, which may be carbon with the encapsulated electrochemically active species immobilised on it. There will also be a counter electrode and there may also be a reference electrode, with the three electrodes being in contact with an electrolyte solution which may be aqueous or non-aqueous. The electrodes may be separate from each other but it may be convenient that a sensor incorporates the working electrode, the counter electrode and any reference electrode within a single structure.

Sensors embodying this invention may be employed in a diverse range of applications, including equipment for testing aqueous fluids at the Earth's surface. However, an area of application which is of particular interest to us is in devices for testing subterranean fluids, in particular devices to be used downhole in a well.

Downhole measurement tools for oilfield applications are known as such. An electro-chemical technique using a sensor in accordance with the present invention can be applied for example as part of a production logging tool or an open hole formation tester tool for use in a well drilled for oil or gas. In such a case, the invention may be used in providing a downhole real-time water sample validation or downhole pH or sulfide measurement which in turn can be used for predicting mineral scale and for corrosion assessment. Such tools may be devices lowered into a well by means of a cable, such as wireline or slickline, or may be tools carried into a well by coiled tubing, or even tools which are positioned downhole for a longer period.

Downhole measurement tools are also used in wells drilled to monitor groundwater or to access subterranean aquifers. A sensor in accordance with the invention can be utilised in such tools, notably in providing real time measurement of pH and/or oxygen content.

These and other features of the invention, preferred embodiments and variants thereof, possible applications and advantages will become appreciated and understood by those skilled in the art from the following detailed description and drawings.

BRIEF DESCRIPTION OF THE DRAWINGS

FIG. 8 is a diagrammatic cross section of a sensor unit embodying the invention;

FIG. 9 is a diagrammatic illustration of a wireline tool incorporating the sensor unit of FIG. 8;

FIG. 10 is a diagrammatic illustration of a cable-suspended tool for testing water.

DETAILED DESCRIPTION AND EXAMPLES

Example 1

Encapsulation of Hydrophobic Redox Chemical

Figure 1:
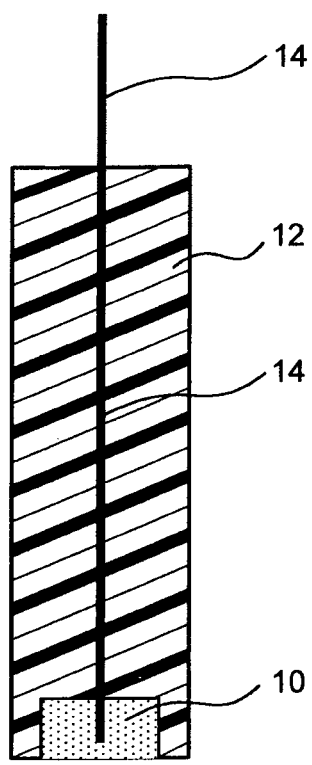
FIG. 1 is a diagrammatic cross-section of a sensor with a carbon paste electrode containing polymer particles.

Anthraquinone was encapsulated in polysulfone (PSU) from Sigma-Aldrich Chemicals. This polymer has the formula

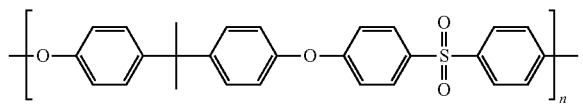

It was stated to have a number average molecular weight $M_n$ of approximately 22,000 and a glass transition temperature of 190° C. The organic solvent which was used was dichloromethane ($CH_2Cl_2$). Polyvinyl alcohol (80% hydrolysed polyvinyl acetate) was used as an emulsifier.

Anthraquinone (0.03 gm) and encapsulating polymer (0.20 gm) were dissolved in 10 ml dichloromethane. These amounts were calculated to lead to polymer particles containing 12-13 wt % anthraquinone. Polyvinyl alcohol (0.375 gm) was dissolved in de-ionised water (150 gm) using a mechanical stirrer with four vertical blades (Heidolph RZ2050 electronic, 320 rpm) for about 30 min and the solution of dye and polymer in dichloromethane was then added to it, dropwise, to form an emulsion of the dichloromethane solution in the water. This emulsion was stirred at 320 rpm for 2 hours, the time for the dichloromethane solvent to evaporate. The resulting suspension of particles was then poured into 600 ml of de-ionised water and stirred for another 2 hours. These particles were then recovered by vacuum filtration on a cellulose nitrate membrane filter of 0.45 micron pore size and washed thoroughly with water until no coloration of the filtrate water was observed. The particles were then dried for 2 days in a vacuum desiccator and stored in a refrigerator at 4° C.

The same procedure was used to encapsulate ferrocene in polysulfone and also polyvinylferrocene in polysulfone. It was also used to encapsulate ferrocene in two other polymers which were poly-L-lactic acid (PLLA) having a mean molecular weight of 100,000 and a Tg of 51° C. and polystyrene-co-maleic anhydride (PSMA) having a mean molecular weight of 100,000 and a Tg of 120° C. both from Sigma-Aldrich Chemicals.

Median particle sizes were determined using a Malvern Mastersizer. All the particles prepared in this example were found to have median particle sizes $d_{50}$ within a range from 50 to 250 micron. Scanning electron microscopy showed the particles to be spherical with a smooth surface.

Example 2

Encapsulation of Hydrophilic Redox Chemicals

Anthraquinone-2-sulfonic acid, sodium salt (more conveniently referred to as anthraquinone sulfonate) from Sigma-Aldrich Chemicals was encapsulated with polysulfone by the following procedure.

A saline solution of polyvinyl alcohol was prepared by dissolving polyvinyl alcohol (0.375 gm) in water (150 gm) containing 3 wt % sodium chloride using a four bladed mechanical stirrer (Heidolph RZ2050 electronic, 320 rpm) for about 30 min.

Encapsulating polymer (0.20 gm) was dissolved in 3.7 ml dichloromethane and added to a solution of anthraquinone sulfonate (0.03 gm) in water (0.20 ml). The amounts of materials were calculated to lead eventually to particles containing 12-13 wt % anthraquinone sulfonate. The resulting mixture was stirred using a magnetic stirrer at its maximum rate for 10 min to form a water-in-oil emulsion which was then added dropwise to the saline solution of polyvinyl alcohol over about 3 hours with continued stirring to form a water-in-oil-in-water double emulsion. This double emulsion was then poured into 600 ml of water containing 3 wt % sodium chloride and stirred at 320 rpm for another hour. As the dichloromethane solvent evaporated, the dispersed droplets were converted to particles comprising anthraquinone sulfonate encapsulated within polysulfone. The particles were recovered by vacuum filtration on a cellulose nitrate membrane filter of 0.45 micron pore size and washed three times with water. The particles were then dried under vacuum and stored in a refrigerator.

The same procedure was used to encapsulate N,N'-diphenyl-p-phenylenediamine (DPPD), potassium ferrocyanide and t-butylferrocene sulfonate (prepared as described in Tustin et al Journal of Organometallic Chemistry vol 692 pp 5173-5182 (2007)) in polysulfone and was also used to encapsulate t-butylferrocene sulfonate in polystyrene-co-maleic anhydride.

Median particle sizes were determined using a Malvern Mastersizer. All the particles prepared in this example were found to have median particle sizes in a range from 50 to 250 micron. Scanning electron microscopy showed the particles to be smooth and spherical. The same procedure was also used to encapsulate the water soluble dye, ethyl orange, within PLLA. Examination of the resulting particles under an optical microscope showed that each particle contained islands of the ethyl orange in a matrix of the encapsulating polymer.

The redox chemicals which were encapsulated as described in the above two examples are summarised in the following table:

| Encapsulated species | Method | Polymer |
| --- | --- | --- |
| anthraquinone | Example 1 | polysulfone |
| ferrocene | Example 1 | polysulfone, PLLA, PS-MA |
| polyvinylferrocene (PVF) | Example 1 | polysulfone |
| t-butylferrocene sulfonate | Example 2 | polysulfone, PS-MA |
| diethyl-p-phenylenediamine | Example 2 | polysulfone |
| anthraquinone sulfonate | Example 2 | polysulfone |
| potassium ferrocyanide | Example 2 | polysulfone |

Preparation of Carbon Paste Electrodes

A standard procedure was used to prepare carbon paste electrodes containing particles prepared as in the above examples. The particles and graphite in a 1:3 ratio by weight were mixed together in a pestle and mortar to form a homogeneous mixture. Mineral oil was then added and ground together with the mixed solids to produce paste containing 25 wt % mineral oil. It was found to be important to keep close to the 3:1 solids: oil weight ratio because too much mineral oil results in a non-conducting material and too much powder makes the mixture brittle and unstable.

As shown in FIG. 1, a quantity of this paste 10 was packed into a cavity at one end of a cylindrical, electrically insulating, body 12 made of the engineering polymer polyether ether ketone (PEEK). A connecting wire 14 extended through the body 12 from the cavity packed with the paste 10.

The properties of one-electrode sensors prepared in this way were examined by voltammetry experiments with the carbon paste electrode serving as the working electrode (also termed the measuring electrode) in a potentiometric cell. The theory of voltammetry and its application to measurements are both well developed. The subject is discussed in WO 2005/066618 above and is covered in standard textbooks, such as A J Bard and L Faulkner "Electrochemical Methods: Fundamentals and Applications" (2nd ed 2001).

Figure 2:
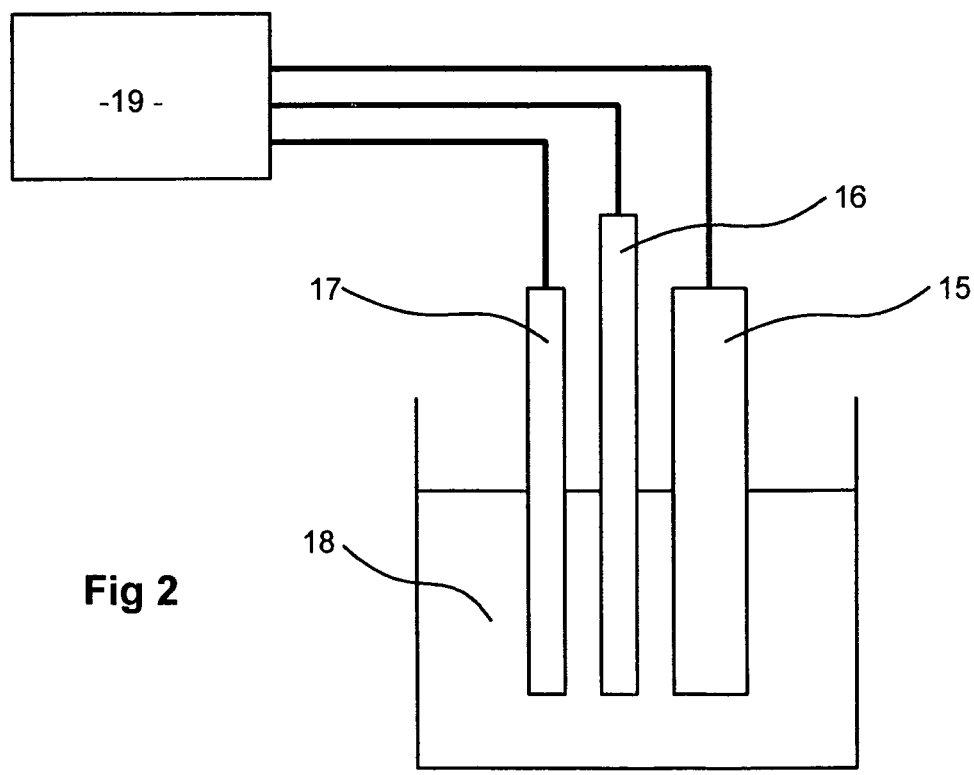
FIG. 2 shows the electrode in a potentiometric cell.

In the examples which follow, a sensor 15 as shown in FIG. 1 was the working electrode. A separate reference electrode 16 and a counter electrode 17 were placed in contact with a test solution 18, thus forming a potentiometric cell as shown in FIG. 2. All three of these electrodes were joined by electrically insulated connections to a potentiostat 19 which is able to apply a variable potential difference between the working electrode provided by the sensor 15 and the counter electrode 17. The potentiostat 19 was used to carry out voltammetry experiments, measuring and recording the current flow as the applied potential was varied. Suitable potentiostats are available from Eco Chemie BV, Utrecht, Netherlands. In these experiments the counter electrode was a 1 mm diameter platinum wire and the reference electrode was a standard calomel electrode.

Example 3

Figure 3:
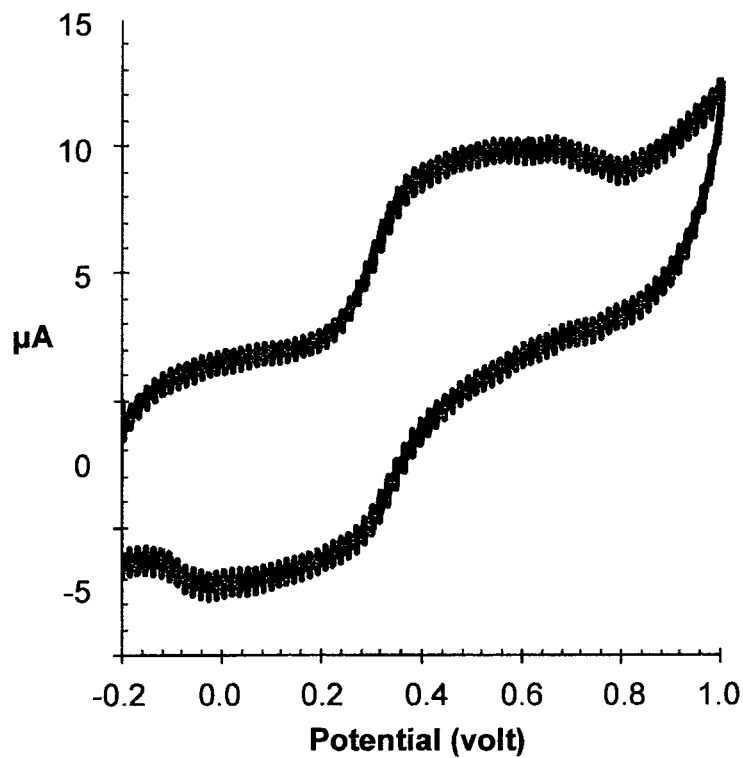
FIG. 3 shows the cyclic voltammetric signal obtained with a carbon paste electrode comprising particles in which t-butylferrocene sulfonate was encapsulated with polysulfone.

A sensor as illustrated in FIG. 1 incorporating a carbon paste electrode containing particles comprising t-butylferrocene sulfonate encapsulated within polysulfone (PSU) was subjected to cyclic voltammetry in pH 7 buffer solution. The resulting signal is shown in FIG. 3. An oxidation wave along with a corresponding reduction wave were observed at +0.50 V and +0.10 V respectively. Analysis of the peak to peak separation for the encapsulated particle showed that it is similar to that of t-butylferrocene sulfonate dissolved directly in aqueous media as reported by Tustin et al Journal of Organometallic Chemistry vol 692 pp 5173-5182 (2007). This therefore indicates that hydrogen ions were diffusing through the polysulfone layer.

Example 4

Figure 4:
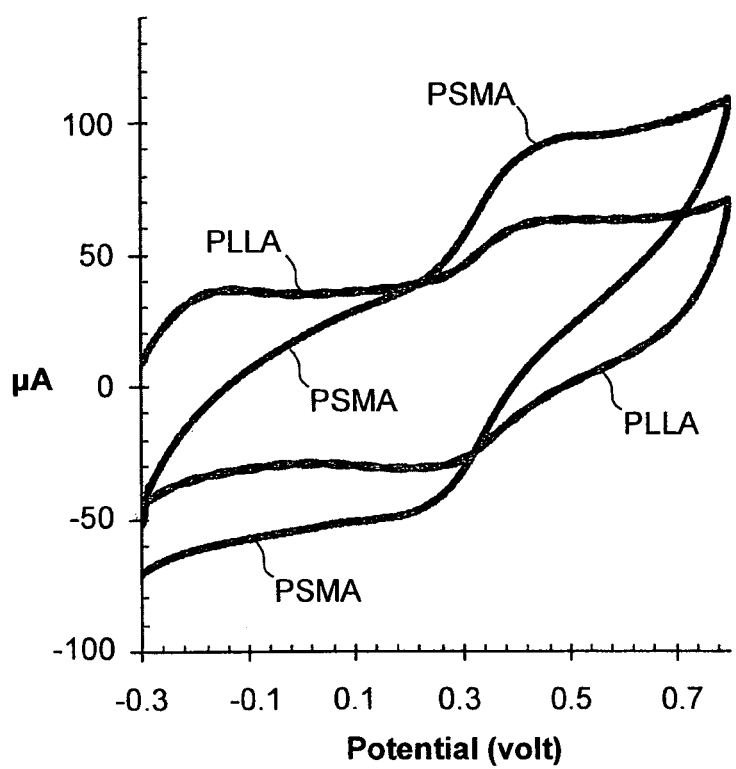
FIG. 4 shows the corresponding signals obtained when t-butylferrocene sulfonate was encapsulated with two other polymers.

The experiment of the above example was repeated using particles in which the encapsulating polymer was PSMA and then repeated again using particles in which the encapsulating polymer was PLLA. The resulting signals are shown in FIG. 4.

Example 5

Figure 5A:
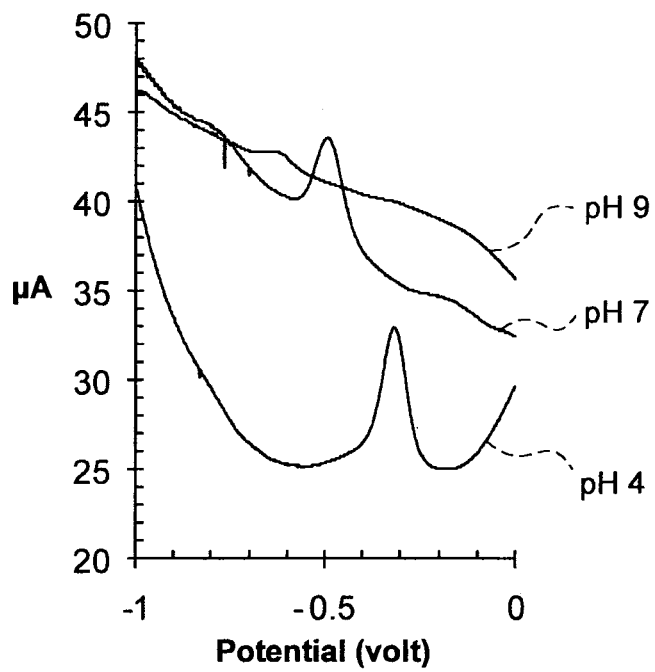
FIG. 5A shows the square wave voltammetric response obtained in three buffer solutions with a carbon paste electrode comprising particles in which anthraquinone sulfonate was encapsulated with polysulfone.
Figure 5B:
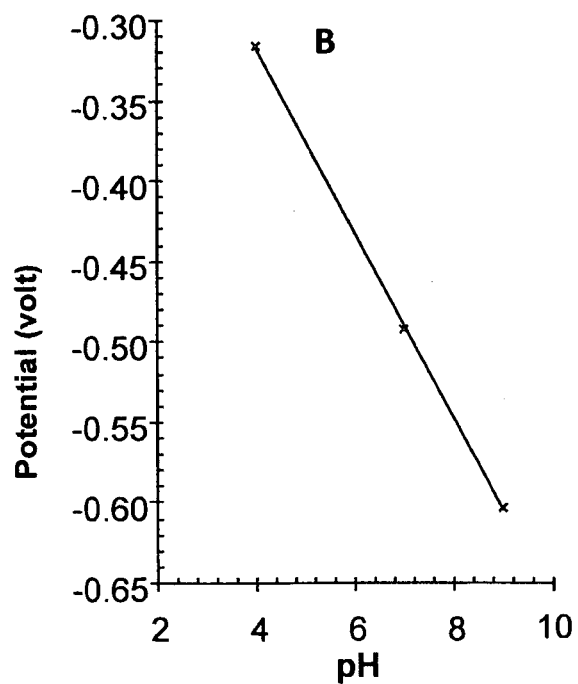
FIG. 5B shows peak potential plotted against pH for the voltammetry signals shown in FIG. 5A.

A sensor as illustrated in FIG. 1 incorporating a carbon paste electrode containing particles comprising anthraquinone sulfonate encapsulated within polysulfone (PSU) was subjected to square wave voltammetry in buffer solutions at pH 4, 7 and 9. The resulting signals are shown in FIG. 5A. These signals show a well resolved oxidation wave whose potential varies with pH from −0.31 V (pH 4) to +0.60 V (pH 9). A plot of oxidative peak potential as a function of pH (FIG. 5B) was found to be linear with a gradient of 58 mV/pH unit consistent with an n electron, n proton oxidation process where n is likely to be 2. This indicates that the hydrogen ions can pass through the polymer layer to the encapsulated particle and therefore the redox chemistry of the encapsulated species mimics that of the species in solution.

Example 6

Figure 6:
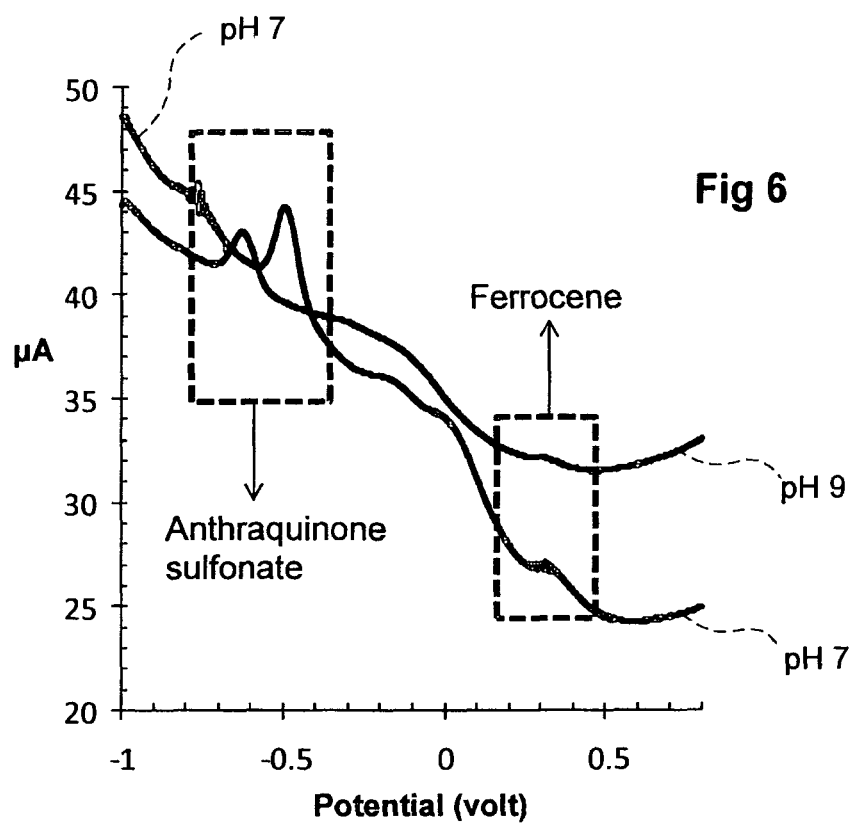
FIG. 6 shows the square wave voltammetric response obtained in two buffer solutions with a carbon paste electrode comprising two types of particles.

A mixture of particles comprising ferrocene encapsulated within polysulfone and particles comprising anthraquinone sulfonate encapsulated within polysulfone was mixed with graphite and used to make a sensor of the kind illustrated in FIG. 1 with a carbon paste working electrode in which both these kinds of particles were present. This electrode was examined by square wave voltammetry as in Example 5 using buffer solutions at pH 7 and pH 9. The resulting signals are shown in FIG. 6. It can be clearly seen that at each pH two redox active waves are observed, the first at lower pH (anthraquinone sulfonate) varies with pH whilst the second at higher pH (ferrocene) is independent of pH. Such an electrode, containing particles whose electrochemical response is pH dependent together with other particles whose response is pH independent could be used in a pH sensor. The pH independent species serves as an internal reference and the variation in potential of the pH dependent peak provides a measure of pH.

Example 7

Figure 7:
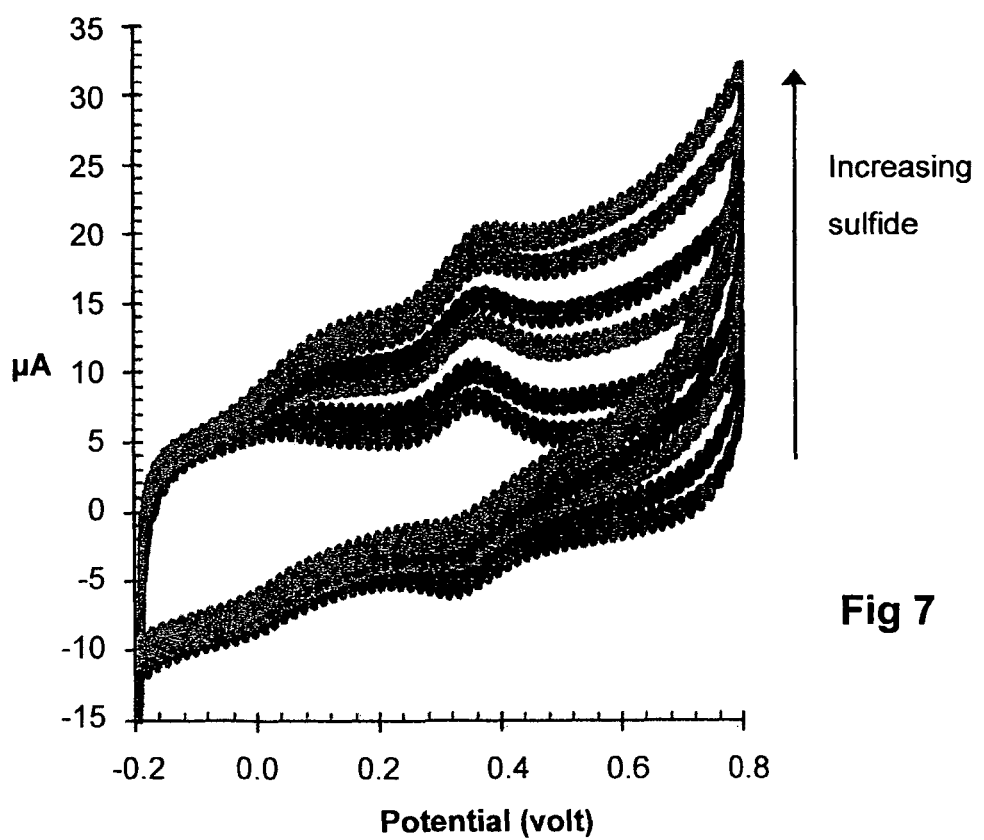
FIG. 7 shows cyclic voltammetric signals obtained with a carbon paste electrode and a progressively increasing concentration of sulfide in the test solution.

A sensor as illustrated in FIG. 1 incorporating a carbon paste electrode containing particles comprising t-butylferrocene sulfonate encapsulated within polysulfone (PSU) was subjected to cyclic voltammetry in pH 7 buffer solution. In a succession of experiments increasing amounts of sulfide were added to the test solution so that the sulfide concentration ranged from zero to 0.5 mM sulfide. The signals obtained are shown in FIG. 7. It can be seen that the current flow increased progressively with the concentration of sulfide and the peak of the oxidation wave shifted from +0.3 volts to +0.4 volts.

Apparatus

FIG. 8 illustrates in cross section a sensor unit embodying the invention. It has a main body 32 which is cylindrical. This body is intended to be accommodated inside a cylindrical cavity in a wellbore tool or other structure and is encircled by two sealing rings 34 to provide a seal between the body 32 and the cavity accommodating it. The body 32 supports a working electrode 40, and a counter electrode 42. Electrical connections to the electrodes are indicated at 46. Immobilised at the exposed surface 41 of the electrode 40 are particles of polymer encapsulating redox systems such as those described in Examples 3 to 7 above. This surface 41 and an end portion of the counter electrode 42 are in contact with an electrolyte retained by a membrane 44 within a cavity 48 at the end of the body 32. This membrane 44 separates the electrolyte from the fluid under test, but is permeable to the species such as hydrogen ($H^+$) ions and bisulfide ($HS^-$) whose concentration is to be measured. Depending on the nature of the fluid under test, it may be possible to dispense with the membrane 44 and allow the surface 41 and counter electrode 42 to contact the test fluid directly.

FIG. 9 diagrammatically illustrates a wireline tool with a generally cylindrical body 52 suspended at the lower end of a wireline 54. The body 52 is provided with centralisers 56 for positioning it within a wellbore. The body 52 may house a variety of devices for making measurements on the wellbore, the surrounding geological formation and on fluid within the wellbore. Amongst these is a sensor unit 60 such as that of FIG. 8. This is fitted into a cavity within the body 52 so that the end 49 of the sensor unit 60 is exposed to the fluid within the wellbore. The tool body 52 also encloses a unit 62 for supplying voltage to the electrodes of the sensor unit 60, measuring the current which flows and communicating the results to the surface via the wireline cable.

A wireline tool such as that diagrammatically illustrated by FIG. 9 could be configured and used to determine the producing zones of an oil production well. For vertical and near vertical wells, the tool is suspended from the wireline cable which is used to lower and raise the tool within the well. For highly deviated wells, the tool is pushed or pulled using coiled tubing from the surface, or a tractor powered and controlled by cable from the surface.

In analogous manner a wireline tool could be configured and used to investigate an underground body of water contacted by a well drilled into an aquifer.

A sensor in accordance with this invention could also be incorporated into a wide variety of other tools and equipment. Possibilities include use in tools which are located permanently downhole, use in tools which are conveyed downhole at the head of coiled tubing, use in underground, undersea or surface pipeline equipment to monitor liquid flowing in the pipeline, and use in various kinds of process plant at the Earth's surface. A sensor in accordance with this invention may well be used outside the oil and gas industry. Use in water treatment can be envisaged, as can use in a wide variety of other areas of science and industry.

FIG. 10 illustrates a tool for investigating subterranean water. This tool also has a cylindrical body 52 which is suspended from a cable 55. A sensor unit 60 is accommodated within the body so that its end 49 is exposed to the subterranean water. The tool also encloses also encloses a unit 62 for supplying voltage to the electrodes of the sensor unit 60, measuring the current which flows and transmitting the results to the surface.

The invention claimed is:

1. A method of measuring an analyte concentration in a fluid which comprises
    exposing an electrochemical sensor to the fluid, where the sensor comprises at least one electrode and at least one electrochemically active species able to undergo reversible electrochemical reduction and oxidation reaction in response to electrical potential applied to the electrode, said reaction being modified by the presence of an analyte species, and
    applying varying potential to the sensor to bring about the reduction or oxidation reaction while observing current flow;
    wherein the said electrochemically active species is encapsulated within separate polymer particles and analyte molecules pass through the separate polymer particles for the redox reaction to take place inside the encapsulation.

2. A method according to claim 1 wherein the encapsulating polymer has a glass transition temperature above the temperature of the fluid.

3. A method according to claim 1 wherein the sensor comprises a solid substrate to which at least one said encapsulated electrochemically active species is immobilized.

4. A method according to claim 3 wherein the substrate is electrically insulating and the encapsulated species is immobilized proximate to a said electrode.

5. A method according to claim 3 wherein a said electrode comprises an electrically conductive solid body and the encapsulated species is immobilized thereon.

6. A method according to claim 3 wherein the electrically conductive substrate comprises carbon.

7. A method according to claim 1 wherein the sensor comprises at least one further electrode which is electrically insulated from the first said electrode.

8. A method according to claim 1 wherein the polymer has a glass transition temperature above 80° C.

9. A method according to claim 1 wherein the polymer has a glass transition temperature above 120° C.

10. A method according to claim 1 wherein the electrochemically active species is/are one or more molecules capable of undergoing reversible oxidation and reduction reactions brought about through application of electrical potential to the electrodes.

11. A method according to claim 10 wherein an oxidation and or reduction reaction displays a potentiometric shift dependent on concentration of an analyte.

12. A method according to claim 11 wherein the analyte is hydrogen ion or bisulfide ion.

13. A method according to claim 10 comprising at least two encapsulated species capable of undergoing reversible oxidation and reduction reactions brought about through application of electrical potential to the electrodes, where a said oxidation and/or reduction reaction of one species displays a potentiometric shift dependent on concentration of an analyte and a said oxidation and/or reduction reaction of another species takes place at a potential which is independent of the concentration of that analyte.

14. A method according to claim 1 wherein the polymer particles comprise a multiplicity of islands of the electrochemically active species, distributed within a continuous matrix of the polymer.

15. A method according to claim 1 wherein the sensor comprises an insulating body, at least two electrodes supported by the body and electrically insulated from each other and at least one electrochemically active species able to undergo electrochemical reaction in response to electrical potential applied to the electrodes, said reaction being modified by the presence of an analyte species, wherein the polymer particles in which the at least one said electrochemically active species is encapsulated are immobilized relative to the insulating body.

16. A method according to claim 1 carried out at a location below ground.

17. A method according to claim 1 carried out downhole in a wellbore.

18. A method according to claim 1 wherein the polymer comprises benzene rings joined through sulfone groups.

* * * * *